US009844326B2

(12) United States Patent
Banerjee et al.

(10) Patent No.: US 9,844,326 B2
(45) Date of Patent: Dec. 19, 2017

(54) SYSTEM AND METHODS FOR CREATING REDUCED TEST SETS USED IN ASSESSING SUBJECT RESPONSE TO STIMULI

(75) Inventors: Bonny Banerjee, Palm Bay, FL (US); Lee Stanley Krause, Indialantic, FL (US); Alice Holmes, Gainesville, FL (US); Rahul Shrivastav, Gainesville, FL (US)

(73) Assignees: UNIVERSITY OF FLORIDA RESEARCH FOUNDATION, INC., Gainesville, FL (US); COCHLEAR LIMITED, Macquarie University (AU)

( * ) Notice: Subject to any disclaimer, the term of this patent is extended or adjusted under 35 U.S.C. 154(b) by 1472 days.

(21) Appl. No.: 12/201,492

(22) Filed: Aug. 29, 2008

(65) Prior Publication Data
US 2010/0056950 A1    Mar. 4, 2010

(51) Int. Cl.
A61B 5/00    (2006.01)
A61B 5/12    (2006.01)
H04R 25/00    (2006.01)

(52) U.S. Cl.
CPC .............. *A61B 5/121* (2013.01); *H04R 25/70* (2013.01); *H04R 2225/43* (2013.01)

(58) Field of Classification Search
CPC ..... A61B 5/121; H04R 2225/43; H04R 25/70
USPC ....................... 73/585; 381/329, 60; 600/559
See application file for complete search history.

(56) References Cited

U.S. PATENT DOCUMENTS

| 4,049,930 A | 9/1977 | Fletcher et al. |
| 4,327,252 A | 4/1982 | Tomatis |
| 4,953,112 A | 8/1990 | Widin et al. |
| 5,008,942 A | 4/1991 | Kikuchi |
| 5,785,661 A | 7/1998 | Shennib |
| 6,035,046 A | 3/2000 | Cheng et al. |
| 6,036,496 A | 3/2000 | Miller et al. |
| 6,118,877 A | 9/2000 | Lindemann et al. |
| 6,446,038 B1 | 9/2002 | Bayya et al. |
| 6,684,063 B2 | 1/2004 | Berger et al. |
| 6,763,329 B2 | 7/2004 | Brandel et al. |
| 6,823,171 B1 | 11/2004 | Kaario |
| 6,823,312 B2 | 11/2004 | Mittal et al. |
| 6,913,578 B2 | 7/2005 | Hou |

(Continued)

FOREIGN PATENT DOCUMENTS

| EP | 1519625 | 3/2005 |
| JP | 2002/291062 | 10/2002 |
| WO | WO-98/44762 | 10/1998 |
| WO | WO-99/31937 | 6/1999 |

(Continued)

OTHER PUBLICATIONS

Fujisaki, et al., "Auditory Perception of Duration of Speech and Non-Speech Stimuli," dated 1973, pp. 45-64.

(Continued)

*Primary Examiner* — Michael C Stout
(74) *Attorney, Agent, or Firm* — Merchant & Gould P.C.

(57) ABSTRACT

A computer-implemented method for generating a test set for testing a subject using a computer system comprising logic-based processing circuitry is provided. The method includes the step of selecting one or more features from among a plurality of features, wherein a measurable effect on the subject of each feature selected is based on a predetermined threshold. The method also includes generating one or more classes of stimuli based on the selected features. The method further includes selecting stimuli from one or more of said classes for presenting to the subject.

25 Claims, 3 Drawing Sheets

(56) References Cited

U.S. PATENT DOCUMENTS

| | | |
|---|---|---|
| 6,914,996 B2 | 7/2005 | Takeda |
| 7,206,416 B2 | 4/2007 | Krause et al. |
| 2002/0120440 A1 | 8/2002 | Zhang |
| 2002/0138272 A1 | 9/2002 | Bennett et al. |
| 2003/0007647 A1 | 1/2003 | Nielsen et al. |
| 2005/0027537 A1 | 2/2005 | Krause et al. |
| 2007/0286350 A1 | 12/2007 | Krause et al. |
| 2009/0024183 A1* | 1/2009 | Fitchmun ........... A61N 1/36032 607/56 |

FOREIGN PATENT DOCUMENTS

| | | |
|---|---|---|
| WO | WO-01/84538 | 11/2001 |
| WO | WO-2004/080532 | 9/2004 |
| WO | WO-2005/062766 | 7/2005 |
| WO | WO-2007030402 | 3/2007 |
| WO | WO-2008081446 | 7/2008 |

OTHER PUBLICATIONS

International Search Report for International Application No. PCT/US2009/055348, dated from the International Search Authority on Apr. 23, 2010, 5 pgs.

Runkle et al. "Active Sensory Tuning for Immersive Spatialized Audio," ICAD, 2000, 4 pages.

International Search Report for PCT Appl. No. PCT/US04/19843, dated Mar. 22, 2006, 2 pages.

Written Opinion for PCT Appl. No. PCT/US04/19843, dated Mar. 22, 2006, 5 pages.

Examination Report for European Patent Appl. No. 04755788.9, dated Nov. 18, 2009, 4 pages.

International Search Report for PCT Appl. No. PCT/US09/55348, dated Aug. 23, 2010, 5 pages.

Written Opinion for PCT Appl. No. PCT/US09/55348, dated Aug. 23, 2010, 10 pages.

International Search Report for PCT Appl. No. PCT/US2010/029020, dated Jul. 12, 2010, 3 pages.

Written Opinion for PCT Appl. No. PCT/US2010/029020, dated Jul. 12, 2010, 7 pages.

International Search Report for PCT Appl. No. PCT/US2010/029021, dated Jul. 16, 2010, 3 pages.

Written Opinion for PCT Appl. No. PCT/US2010/029021, dated Jul. 16, 2010, 7 pages.

Jakobson et al. "Preliminaries to Speech Analysis, The Distinctive Features and their Correlates" The MIT Press, Nov. 1961, cover page and p. 43 (2 pages provided).

* cited by examiner

SYSTEM AND METHODS FOR CREATING REDUCED TEST SETS USED IN ASSESSING SUBJECT RESPONSE TO STIMULI

FIELD OF THE INVENTION

The present invention is related to the field of subject testing, and more particularly, to techniques for creating effective and efficient test sets for testing a selected capability of a subject, such as a patient, based on the subject's response to administered stimuli.

BACKGROUND OF THE INVENTION

Subject testing arises in a wide variety of contexts and ranges from posing a battery of test questions to eliciting a subject's response to different types of stimuli. A prime example of the latter type of testing is the technique used to fit a hearing-impaired subject, or patient, with a cochlear implant system. Once a such a system is implanted, as with many other types of digital hearing-enhancement systems, a suitable speech coding and mapping strategy must be selected to enhance the performance of the system for day-to-day operation. The mapping strategy pertains to an adjustment of parameters corresponding to one or more independent channels of a multi-channel cochlear implant or other hearing-enhancement system. Selection of each strategy typically occurs over an introductory period of approximately six or seven weeks, during which the hearing-enhancement system is tuned for the particular patient. During this tuning period, users of such systems are asked to provide feedback on how they feel the device is performing.

More particularly, to create a mapping for a speech processor, an audiologist first determines the electrical dynamic range for each electrode or sensor used. The programming system delivers an electrical current through the hearing-enhancement system to each electrode in order to obtain the electrical threshold (T-level) and comfort or "max" level (C-level) measures defined by a system's manufacturer. T-level, or minimum stimulation level, is the minimum electrical current capable of producing an auditory sensation in the user 100 percent of the time. The C-level is the loudest level of signal to which a user can listen comfortably for a long period of time.

A speech processor then is programmed or "mapped" using one of several encoding strategies so that the electrical current delivered to the implant will be within this measured dynamic range; that is between the T- and C-levels. After T- and C-levels are established and the mapping is created, the microphone is activated so that the patient is able to hear speech and other sounds. From that point onwards, the tuning process continues as a traditional hearing test. Hearing-enhancement device users are asked to listen to tones of varying frequencies and amplitudes. The gain of each channel can be further altered within the established threshold ranges such that the patient is able to hear various tones of varying amplitudes and frequencies reasonably well.

Not surprisingly, fitting and tuning a hearing-enhancement system of any type so as to meet the needs of a particular patient is typically quite costly and very time consuming, both from the perspective of the hearing-impaired patient and the audiologist. The functions of such a system are regulated by a large number of parameters, values for each of which typically must be determined so as to tune the system to provide optimal performance for the particular patient. In order to do so, the patient typically must be thoroughly tested with respect to each of set of parameter values. The number of tests generally increases exponentially as the number of system parameters increases.

More generally, the problems inherent in testing a hearing-impaired patient so as to optimally set the system parameters values for a hearing-enhancement system arise with various other types of qualitative or quantitative tests in which a subject has to respond to posed test questions or physical stimuli. Many testing techniques, such as those utilized for tuning a hearing-enhancement system as described above, require a substantial investment of time and effort. Accordingly, there is a need for a technique that in such contexts is able to reduce testing time without compromising the quality of the testing performed.

SUMMARY

With the foregoing background in mind, it is therefore a feature of the invention to provide systems and methods for reducing time and effort expended in testing a subject without compromising the quality of the results yielded from the testing. One aspect of the invention is to provide systems and methods that utilize techniques for identifying the raw perceptual weaknesses of a subject in a considerably shortened time frame as compared to conventional techniques.

One embodiment is a computer-based system for generating a test set for testing a subject. The system can include one or more processors and an electronic memory having stored therein electronic data representing a plurality of features for testing a particular capability of the subject. The system can include a feature-selecting module configured to execute on the one or more processors for selecting one or more features from among the plurality of features, wherein a measurable effect on the subject of each feature selected exceeds a predetermined threshold. The system also can include a stimulus-selecting module configured to execute on the one or more processors for generating one or more classes of stimuli based upon the selected feature, and selecting at least one stimulus from each class for presenting to the subject. The stimulus-selecting module can be further configured to initially choose each stimulus from each class to present to the subject, and subsequently select at least one less from each class that comprises more than one stimulus. At least one of the stimuli subsequently selected from each class that comprises more than one stimulus can be selected randomly by the stimulus-selecting module.

Still another embodiment is a computer-based system of testing a hearing-impaired patient. The system can include an audio unit for audibly presenting a plurality of phonemes to the patient, wherein each phoneme is selected from one of a plurality of phoneme sets corresponding to a predetermined feature selected for testing a hearing capability of the patient. The system further can include a testing unit comprising at least one processor for generating a first assessment of the hearing capability of the patient based upon a response of the patient to each audibly presented phoneme. Moreover, the system can audibly present a second plurality of phonemes to the patient and generate a second assessment of the hearing capability of the patient based upon patient response. The second plurality of phonemes can be selected by the testing unit choosing at least one less phoneme from each phoneme set that contains more than one phoneme, one of the phonemes selected from each phoneme set containing more than one phoneme being selected randomly.

Still another embodiment is a computer-implemented method for generating a test set for testing a subject using a computer system comprising logic-based processing circuitry. The method can include selecting one or more features from among a plurality of features, the selecting comprising selecting one or more feature having a measurable effect on the subject, as determined based on a predetermined threshold. The method also can include generating one or more classes of stimuli based on the selected features. The method can further include selecting stimuli from one or more of the classes for presenting to the subject.

Yet another embodiment of a method for generating a test set for testing a subject using a computer system comprising logic-based processing circuitry includes selecting one or more features from among a plurality of features, wherein a measurable effect on the subject of each feature selected exceeds a predetermined threshold. The method can further include generating, based on the selected features, one or more classes of stimuli. The method further can include selecting stimuli from one or more of the classes for presenting to the subject, wherein selecting comprises choosing a stimulus from a class to present to the subject, and subsequently selecting at least one less from each class that comprises more than one stimulus.

Still another embodiment of the invention is a computer-implemented method for generating a test set for testing a subject using a computer system comprising logic-based processing circuitry. The method can include selecting one or more features from among a plurality of features, wherein a measurable effect on the subject of each feature selected exceeds a predetermined threshold. The method also can include generating one or more classes of stimuli based on the selected features, and selecting stimuli from each class for presenting to the subject. More particularly, the selecting can include initially choosing each stimulus from each class to present to the subject, and subsequently selecting at least one less from each class that comprises more than one stimulus. At least one of the stimuli subsequently selected from each class that comprising more than one stimulus can be selected randomly.

BRIEF DESCRIPTION OF THE DRAWINGS

There are shown in the drawings, embodiments which are presently preferred. It is expressly noted, however, that the invention is not limited to the precise arrangements and instrumentalities shown in the drawings.

DETAILED DESCRIPTION

Figure 1:
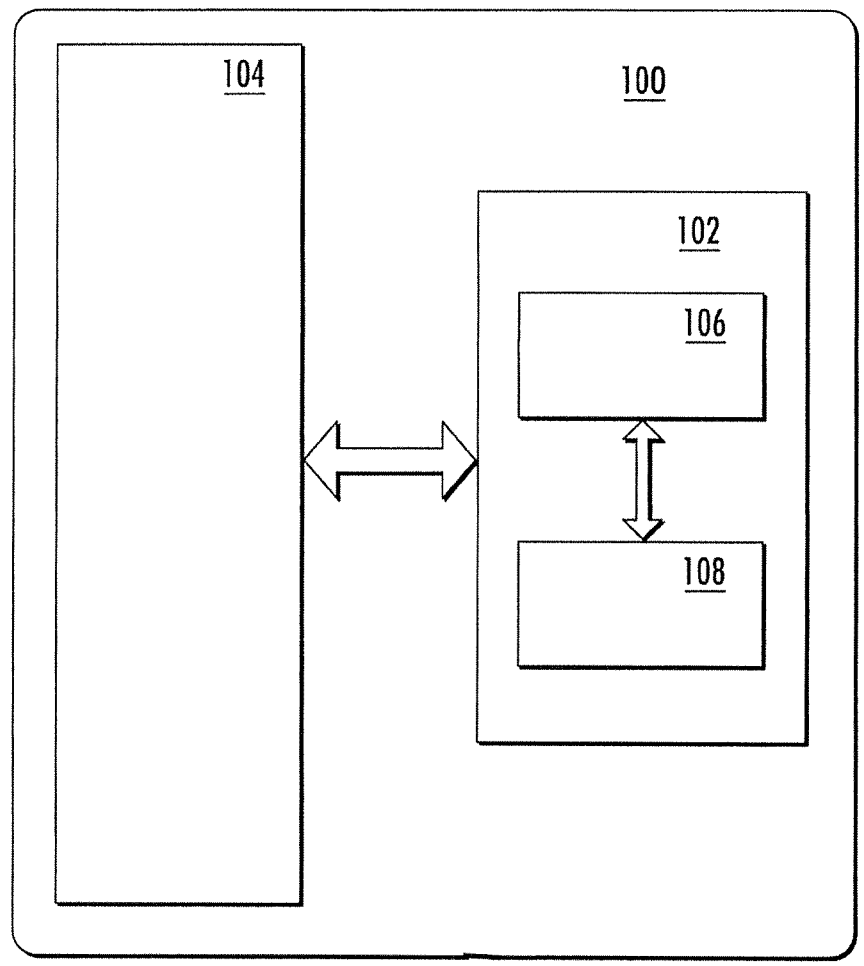
FIG. 1 is a schematic diagram of a system for generating a test set for testing a subject, according to one embodiment of the invention.

Referring initially to FIG. 1, a computer-based system 100 for generating a test set for testing a subject, according to one embodiment, is schematically illustrated. The system 100 illustratively includes one or more processors 102 comprising registers, logic gates, and other data processing circuitry (not explicitly shown) for executing processor-executable instructions. The system 100 also illustratively includes an electronic memory 104 for electronically storing processor-executable instructions and data.

Additionally, the system 100 illustratively includes a feature-selecting module 106, the operative features of which are described more particularly below and which is communicatively linked to the one or more processors 102. The system 100 further illustratively includes a stimulus-selecting module 108, the operative features of which are also described more particularly below. Like the feature-selecting module 106, the stimulus-selecting module 108 is communicatively linked to the one or more processors 102.

Accordingly, each of the feature-selecting module 106 and the stimulus-selecting module 108 can be implemented in a combination of the processing circuitry of the one or more processors and processor-executable instructions that, when loaded to and executed by, one or more processors performs the operations, procedures, and functions described herein. In an alternate embodiment, however, one or both the feature-selecting module 106 and the stimulus-selecting module 108 can be implemented in dedicated hardwired circuitry configured to perform the same operations, procedures and functions. Ones possessing the ordinary skills in the art will also recognize that a combination of processing circuitry, hardware and/or firmware may be utilized to implement the feature-selecting module 106 and the stimulus-selecting module 108.

Operatively, the system 100 stores in the memory 104 electronic data representing a plurality of features for testing a particular capability of the subject. In a preferred embodiment, the feature-selecting module 106 executes on the one or more processors and selects one or more of the features from among the plurality of features. As described more particularly below, the feature-selecting module 106 is configured to select those features that have a significant effect on the subject; that is, each feature selected exceeds a predetermined threshold. The stimulus-selecting module 108 executing on the one or more processors generates one or more classes of stimuli based on the selected feature. As used herein, a stimulus is any signal, question, or other other-response eliciting element that is conveyed to a subject to elicit one or more responses that can be used to determine a capability, condition, or attribute of the subject. Stimuli can be grouped into distinct classes corresponding to one or more features, wherein the features are those attributes associated with certain stimuli. As described herein, the subject's ability to discern certain features when presented with a corresponding stimulus indicates a particular capability or characteristic of the subject.

Subsequently, or simultaneously, in a preferred embodiment, as each class is generated, the stimulus-selecting module 108 selects at least one stimulus from each class for presenting to the subject. The stimulus-selecting module 108 is further configured to initially choose each stimulus from each class to present to the subject, and to subsequently select at least one less from each class that comprises more than one stimulus. According to this embodiment, at least one of the stimuli subsequently selected from each class that comprises more than one stimulus is selected randomly by the stimulus-selecting module 108.

As is described below, a stimulus-selecting module may be presented with fewer than all stimuli if the tester determines a priori that certain stimuli are of lesser significance. Furthermore, the tester may select a stimulus from less than all classes for presenting to a subject if time saving is desired. However, either of these approaches to limiting stimuli or class presentation may compromise the quality of testing.

Stimuli can be used to test particular capabilities of a subject, such as a patient. Specific stimuli can be associated with particular features that characterize the particular capabilities. Thus, generally, the purpose of eliciting a response of the subject to the stimuli is to identify features with respect to which the subject is weak. For example, in the context of testing hearing, two distinctive feature sets have been proposed. The first is based on the articulatory positions underlying the production of speech sounds. The other is based on the acoustic properties of various speech sounds. These properties describe a small set of contrastive acoustic properties that are perceptually relevant for the discrimination of pairs of speech sounds. More particularly, as will be readily understood by one of ordinary skill, the different distinctive features and their potential acoustic correlates can be broadly grouped into three categories: fundamental source features, secondary consonantal source features, and resonance features.

It should be noted that these are not the only ways in which various features can be categorized. There can also be additional features, or groups of features that more optimally describe different tasks. For example, with respect to a different language such as Mandarin using additional features, albeit in accordance with the process described herein, the results can be further enhanced.

The fundamental source features can be further characterized on the basis of whether the speech sounds are vocalic or non-vocalic. Vocalic speech corresponds to speech sounds associated with vowels. Accordingly, such speech sounds correspond to a single periodic source, the onset of the speech not being abrupt; otherwise the speech sound can be characterized as non-vocalic. The fundamental source features also can be characterized on the basis of whether the speech sounds are consonantal or non-consonantal. Consonantal speech sounds correspond to sounds associated with consonants. Such speech sounds are characterized by the presence of zeros in the associated spectrum of the sounds.

The secondary consonantal source features can be further characterized on the basis of whether the speech sounds are interrupted or continuant. Continuant speech sounds, are also characterized as semi-vowels, because of their similar sound quality. There is little or no friction with continuant speech sounds as the air passes out freely through the mouth of the speaker. A continuant speech sound is produced with an incomplete closure of the vocal tract. Interrupted speech sounds, by contrast, end abruptly.

The secondary consonantal features can also be characterized on the basis of whether the speech sounds are checked or unchecked. Checked speech sounds, typified by some Far Eastern and African languages, are characterized by abrupt termination as opposed to gradual decay, whereas unchecked speech sounds are characterized by gradual decay. Additionally, secondary consonantal features can be characterized as strident or mellow. The former typically has an irregular waveform, whereas the latter typically has a smooth waveform. A secondary consonantal feature characterized as mellow also has a wider autocorrelation function relative to a corresponding normalized strident feature. Secondary consonantal features can also be classified according to whether the sound is voiced or voiceless.

The resonance features can be further characterized on the basis of whether the speech sound is compact or diffuse. A compact feature is associated with sound having a relative predominance of one centrally located format region, whereas a diffuse features implies sound having one or more non-central formats. The resonance features can also be characterized as grave or acute. Speech sounds that are characterized as grave are low-frequency dominant low frequency, whereas those characterized as acute are high-frequency dominant. Additionally, resonance features can be characterized as flat or plain, depending on whether the there is a downward shift of some or all formats, typically associated with vowels and a reduction in lip orifice of the speaker.

The resonance features also can be further characterized as sharp or plain, the latter characterizing speech sounds whose second and/or higher formats rise. Moreover, resonance features can also be characterized as tense or lax, depending on the amount and duration of the energy of the sound. The resonance features also can be classified according to whether the speech sound is characterized as having a nasal format or a nasal murmur. The distinctive speech features and their potential acoustic correlates are further described in R. Jakobson, G. M. Fant, and M. Halle, PRELIMINARIES TO SPEECH ANALYSIS: THE DISTINCTIVE FEATURES AND THEIR CORRELATES (MIT Press, Cambridge; 1963), which is incorporated herein by reference in its entirety.

Whereas, in the context of testing hearing vocalic, consonantal, compact, and other of the described features are relevant, in other contexts different features will be found to be important. For example, in testing vision, features such as color intensity, object shape or size, and other visual features are important. Thus, although the system 100 is described primarily in the context of testing hearing, it will be readily apparent from the description herein, that the procedures, processes, and functions performed by the system pertain to other applications for testing a subject, such as a patient.

In a preferred embodiment as described in details below, we use fourteen phonemes from the IOWA test [R. S. Tyler, J. P. Preece, and N. Tye-Murray, *The Iowa Phoneme and Sentence Tests*, Dept. of Otolaryngology-Head and Neck Surgery, The University of Iowa, Iowa City, Iowa, 1986] to represent a patient's hearing ability in terms of the features. These phonemes may be consonants or vowels. The testing might also be carried out using words, sentences, phrases, or other sounds as described in U.S. Pat. No. 7,206,416 to Krause, et al. which is incorporated herein by reference in its entirety.

In general, in any particular context, certain relevant features play a greater role than others in the process of the subject recognizing or otherwise responding to a certain set of stimuli. Moreover, in certain applications (e.g., hearing testing) the capability of the subject with respect to one feature is dependent on the subject's underlying capability with respect to another feature.

A subject weak with respect to a certain class of stimuli, characterized for example by an inability to recognize or respond to the stimuli, is typically weak with respect to one or more of the features associated with that class of stimuli. Generally, the size of test set of stimuli is combinatorial with respect to the number of features. Accordingly, it is advantageous to identify the features that play a significant role in determining the subject's hearing ability. The stimuli can be classified into a smaller number of classes based on the significant features. The number of classes of stimuli increases exponentially with the number of features; if the less significant features are not eliminated, many of the classes will be empty.

Accordingly, the system 100 is configured to identify the vital features so as to reduce the number of stimuli classes and allow each class to contain a meaningful set of stimuli. Also, by emphasizing on the vital features, it is expected that the majority of a subject's weaknesses can be ascertained in a shorter period of time than is conventionally the case. Since the brain of a human being is generally adept at recognizing a stimulus from only partial information, it will be sufficient to rectify the weaknesses caused by the more influential features in, for example, the context of tuning a hearing-enhancement device.

According to one embodiment, the feature-selecting module 106 is configured to determine whether the effect of a feature on a subject exceeds a predetermined threshold according to the following:

$$f_i = \begin{cases} 1 & \text{if } v_i \times m_i > \theta \\ 0 & \text{otherwise} \end{cases}$$

where θ is the predetermined threshold, $v_j$ is the number of different values assumed by the ith feature for representing the effect of the test stimuli (e.g., +1 if the feature is present in the stimulus, −1 if it is absent, and 0 if the feature is irrelevant), $m_i$ is the number of different stimuli influenced by the i-th feature. Accordingly, $f_i$ is a quantitative measure of the role of the ith feature. During testing in a preferred embodiment a threshold value of 7 produced excellent results. However, one of the ordinary skills in the art is to recognize that other threshold values may also be used to produce relevant phoneme discrimination. One of the ordinary skills in the art is to recognize that the feature selecting module can be configured differently such that the effect of the features can be less than a predetermined threshold.

Those features that, according to the determination made by the feature-selecting module 108, are assigned a value of 1, are considered to play a vital role. Thus, the stimuli can be classified based on the important features only.

The stimulus-selecting module 106, according to yet another embodiment, can be configured to determine the significance of the $i^{th}$ class of stimuli. In a test, the number of different stimuli chosen from each class is typically proportional to the significance of that class. More particularly, the stimulus-selecting module 106 can be configured to compute the following measure of significance of a class of stimuli:

$$\overline{p_i} = \begin{cases} \dfrac{1}{n_i}\sum_{j=1}^{n_i} P_{ij} & \text{if } n_i > 0 \\ 0 & \text{otherwise} \end{cases}$$

where $n_i$ is the number of different stimuli in the $i^{th}$ class, and $p_{ij}$ is the significance of the $j^{th}$ stimuli in the $i^{th}$ class on the stimuli-recognition ability of the subject. Therefore, significance of the $i^{th}$ class of stimuli on the recognition ability of a patient is given by the above calculation as performed by the stimulus selecting module 106. One of the ordinary skills in the art is to recognize that the stimuli selecting module can be configured differently to compute a measure of significance.

The generation of a test set (i.e., the selected stimuli), as determined by the system 100 according to one embodiment, then depends on three factors: first, the significance of a class of stimuli, as discussed above; second, the weakness of the subject with respect to particular features (in many settings, the weakness becomes apparent within a few tests, and thus the subsequent presentation of stimuli becomes dependent on the weaknesses); and third, the mitigation of testing error, which according to the present invention is achieved by randomized stimuli selection, as described more particularly below.

With respect to the second factor, the stimulus-selecting module 108 can be configured to quantitatively assess the weakness with respect to one or more features. Specifically, the stimulus-selecting module 108 can be configured to compute the following:

$$s_i = \left\lceil k \times \dfrac{e_i}{\sum_{j=1}^{c} e_j} \right\rceil$$

where $e_i$ is the number of erroneously recognized stimuli from the $i^{th}$ class and k is a constant. One of the ordinary skills in the art is to recognize that the stimuli selecting module can be configured differently to assess the weakness with respect to one or more features.

In the preferred embodiment, the stimulus selecting module is utilized to reduce the number of classes and the number of stimuli. One of the ordinary skills in the art is to recognize that the number of stimuli could be reduced a priori based on perceived lower stimuli significance. However, this may result in compromise of the testing quality.

The operative features of the system 100 are now described in the specific context of generating a test set or selected stimuli for testing the hearing capabilities of a patient. The test set, in turn, can be utilized in fitting or "tuning" a hearing-enhancement device such as a cochlear implant. As already noted, the functions of such a device are regulated by a large number of parameters, values for each of which must be determined so as to tune the device to provide optimal performance for a particular patient. Each parameter is assigned one of many values. Conventional techniques for determining the optimal set of parameter values for each patient are difficult and time consuming. A patient typically must be thoroughly tested in order to ascertain the parameter values that yield optimum device performance for the patient.

The goal of testing the hearing-impaired patient is to ascertain his raw hearing ability independent of context and background knowledge. During testing, a series of consonant phonemes can be presented, as stimuli, and the patient's response assessed so as to identify any weakness in his hearing. Different parameters of the hearing-enhancement device can be adjusted accordingly.

The operative features of the system 100 permit the patient to be tested according to an adaptive method, according to a particular embodiment. During testing, audible renderings of phonemes are presented to the patient, rather than words or phrases. The phonemes are selected from a set of fourteen consonant phonemes. In a preferred embodiment, consonant phonemes are preferably used rather than vowel phonemes, because the latter are typically too easily perceived by a patient and do not reveal sufficient information pertaining to the patient's hearing capability. As now described, the system enables the number of phonemes utilized in testing to be reduced, affording a significant savings in time and resources without compromising the quality of the testing performed.

The patient's strengths and weaknesses are assessed based on the patient's response to phonemes corresponding to the different features represented by each. As already noted, a phoneme is characterized by the presence, absence or irrelevance of a set of nine features: Vocalic, Consonantal, Compact, Grave, Flat, Nasal, Tense, Continuant, and Strident. As described more particularly below, the feature-selecting module 106 can be configured to operate on features arranged hierarchically. Those features higher in the hierarchy are those that potentially have a greater effect because the failure to perceive these features affects the perception of a greater number of phonemes. Thus, those features ranked higher in this hierarchy provide a more comprehensive measure of hearing loss as compared to words or phrases. Each phoneme can be associated with a corresponding percentage of proportional occurrence of the phoneme in the English language. (See, e.g., L. Shriberg and R. Kent, Clinical Phonetics, Boston: Allyn & Bacon (2003), incorporated here in its entirety.)

The presence, absence, and irrelevance of a feature with respect to each phoneme can be can be denoted, respectively, as 1, −1, and 0. The fourteen consonant phonemes used in testing and the corresponding constituent features of each are:

| Phonemes | Vocalic | Cons. | Compact | Grave | Flat | Nasal | Tense | Cont. | Strident |
|---|---|---|---|---|---|---|---|---|---|
| n | −1 | 1 | −1 | −1 | 0 | 1 | 0 | 0 | 0 |
| t | −1 | 1 | −1 | −1 | 0 | −1 | 1 | −1 | 0 |
| s | −1 | 1 | −1 | −1 | 0 | −1 | 1 | 1 | 1 |
| d | −1 | 1 | −1 | −1 | 0 | −1 | −1 | −1 | 0 |
| k | −1 | 1 | −1 | 0 | 0 | −1 | 1 | −1 | −1 |
| m | −1 | 1 | −1 | 1 | 0 | 1 | 0 | 0 | 0 |
| z | −1 | 1 | −1 | −1 | 0 | −1 | −1 | 1 | 1 |
| b | −1 | 1 | −1 | 1 | 0 | −1 | −1 | −1 | 0 |
| p | −1 | 1 | −1 | 1 | 0 | −1 | 1 | −1 | 0 |
| v | −1 | 1 | −1 | 1 | 0 | −1 | −1 | 1 | 0 |
| f | −1 | 1 | −1 | 1 | 0 | −1 | 1 | 1 | 0 |
| g | −1 | 1 | 1 | 0 | 0 | −1 | −1 | −1 | −1 |
| sh | −1 | 1 | 1 | 0 | 0 | −1 | 1 | 1 | 0 |
| j | −1 | 1 | 1 | 0 | 0 | −1 | −1 | −1 | 1 |

The features Vocalic and Consonantal remain the same with respect to all fourteen phonemes. The features Tense, Continuant, and Strident do not make a substantial difference to hearing ability, as has been verified empirically. The following exemplary pseudo-code illustrates a procedure that can be implemented by the feature-selecting module 108 for creating a hierarchy of the nine features: This hierarchy is derived in R. Jakobson, G. Fant, and M. Halle, *Preliminaries to Speech Analysis*, Cambridge, Mass.: The MIT Press, 1963, which is incorporated herein in its entirety.

```
If sound is Vocalic
    Is it Consonantal or Non-consonantal
    If Consonantal → /l/
    If Non-consonantal:
        Is it Compact or Diffuse
        If Compact
            Is it Grave or Acute
            If Grave
                Is it Flat or Plain
                    If Flat → /o/
                    If Plain → /a/
            If Acute → /e/
        If Diffuse
            Is it Grave or Acute
            If Grave
                Is it Flat or Plain
                    If Flat → /u/
                    If Plain → neutral vowel "schewa"
            If Acute → /i/
If sound is Non-vocalic
Is it Consonantal or Non-consonantal
    If Non consonantal
        Is it Tense or Lax
            If Tense → /h/
            If Lax → /#/
    If Consonantal
        Is it Compact or Diffuse
        If Diffuse
            Is it Grave or Acute
            If Grave
                Is it Nasal or Oral
                    If Nasal → /m/
                    If Oral
                        Is it Tense or Lax
                        If Tense
                            Is it Cont./Intr.
                                If Con. → /f/
                                If Intr. → /p/
                        If Lax
                            Is it Cont./Intr.
                                If Con. → /v/
                                If Intr. → /b/
            If Acute
                Is it Nasal or Oral
                    If Nasal → /n/
                    If Oral
                        Is it Tense or Lax
                        If Tense
                            Is it Continuant or Interrupted.
                                If Continuant
                                    Is it Strident or Mellow
```

-continued

```
        If Strident → /s/
        If Mellow → "th" as in THanks
                                                        If Interrupted. → /t/
                                            If Lax
                                                Is it Continuant or
Interrupted.
                                                            If Continuant
                                                              Is it
Strident or Mellow
        If Strident → /z/
        If Mellow → /θ/ as in THat
                                                        If Interrupted. →
/d/
                If Compact
                    Is it Nasal or Oral
                            If Nasal → /ng/
                            If Oral
                                Is it Tense or Lax
                                    If Tense
                                        Is it Continuant or Interrupted
                                            If Interrupted
                                                Is it Strident or Mellow
                                                        If Strident → /ch/
        If Continuant → /sh/ as in "SHoe"
                                                        If Mellow → /k/
as in "CHurch"
                                    If Lax
                                        Is it Continuant or Interrupted
                                            If Continuant → /zh/ as in
"meaSure"
                                            If Interrupted
                                                Is it Strident or Mellow
                                                        If Strident → /dz/
as in "Judge"
                                                        If Mellow → /g/
```

With reference to the earlier-described calculation performed by the stimulus-selecting module 106 to determine the significance of the $i^{th}$ class of stimuli, v(ith feature)=the number of different values assumed by the $i^{th}$ feature for representing the test stimuli. For example, Vocalic assumes only one value, '−1' for all the 14 phonemes. Since it fails to change among different values, v(Vocalic)=0. Tense, for example, assumes three different values, '+1', '−1', '0' for the 14 phonemes, and therefore, v(Tense)=3. Thus, v($i^{th}$ feature)=n−1, if n<2; otherwise v($i^{th}$ feature)=n, where n is the number of values assumed by the $i^{th}$ feature.

The m($i^{th}$ feature)=the number of different stimuli influenced by the $i^{th}$ feature. For example, Nasal can affect at most 4 phonemes; that is, perceiving Nasal incorrectly can affect at most 4 phonemes.

The m($i^{th}$ feature) is dependent on the feature hierarchy, not just on the number of +1, −1 or 0 values assumed for the different phonemes. The feature hierarchy is a tree-like structure with the features occurring at the non-leaf nodes and the phonemes occurring at the leaf nodes. To reach a phoneme at a leaf node, one has to traverse the path (or branches) from the tree top (or root) down to the phoneme. One phoneme can be reached via exactly one path, so if a mistake occurs somewhere in the middle of the path (e.g., +1 is chosen for Nasal instead of −1), then it is impossible to reach that phoneme. More significant features, such as Vocalic and Consonantal, are higher up in the tree-like hierarchy, while the less significant features, such as Continuant and Strident, are at the lower levels.

At lower levels, the tree branches out. As a result, there are many non-leaf nodes at the lower levels that contain Continuant or Strident while there is only one node at the highest level with Vocalic. Therefore, getting Vocalic wrong results in all phonemes on one side of the entire tree being wrong. However, getting Strident wrong results in only a very few phonemes on one side of the tree starting from that non-leaf node being wrong. Thus m(Strident) is much less than m(Vocalic). In other words, m($i^{th}$ feature) calculates the size of the largest number of phonemes on one side of the tree starting from the non-leaf node corresponding to the $i^{th}$ feature.

Bearing this in mind, the described calculations, in this example, yield:

f(vocalic), m=14, v=0→m×v=0
f(cons.), m=14, v=0→m×v=0
f(compact), m=10, v=2→m×v=20
f(grave), m=5, v=3→m×v=15
f(flat), m=14, v=0→m×v=0
f(nasal), m=4, v=2→m×v=8
f(tense), m=2, v=3→m×v=6
f(cont), m=1, v=3→m×v=3
f(strident), m=1, v=3→m×v=3

If the threshold θ is chosen to be 7, then Compact, Grave, and Nasal are the features selected.

Once these three features have been selected, the phonemes are classified based on the values assumed by these three features. Each of these features can assume three values: +1, −1, 0. Thus there can be $3^3$-27 different combinations of the values assumed by the three features. Each unique combination of values of the selected features forms a class. So, the combination −1, 1, 1 is a distinct class and so is the combination −1, 1, −1. Most of these classes do not contain any phoneme. Only five of them do. For example, the class 1, 1, 1 does not contain any phoneme, the class −1, 1, 0.1 contains only 'm', while the class −1, 1, −1 contains {b, p, v, f}.

Alternatively, if there is no concern regarding the perception of irrelevance of a feature, but there is with the presence or absence of the feature, then with the same three features, the minimal testing set will contain at most $3^2=9$ phonemes. In this example, the possible combinations may be, therefore.

| Compact | Grave | Nasal | Phonemes representing combinations |
|---------|-------|-------|-----------------------------------|
| 1       | 1     | 1     | —                                 |
| 1       | 1     | -1    | —                                 |
| 1       | -1    | 1     | —                                 |
| 1       | -1    | 1     | —                                 |
| -1      | 1     | 1     | m                                 |
| -1      | 1     | -1    | {b, p, v, f}                      |
| -1      | -1    | 1     | n                                 |
| -1      | -1    | -1    | {t, s, d, z}                      |

The remaining four phonemes {k, g, sh, j} have three important features as 1, 0, −1. Though that does not belong to any of the eight combinations sought, one of them can be used to test for <1 1−1> or <1−1 −1>, especially given that there is no phoneme that has any of these two combinations. Thus, a minimal set of consonant phonemes contains five phonemes—m, n, and one each from the subsets {b, p, v, f}, {t, s, d, z}, and {k, g, sh, j}. The set is devoid of redundancy with respect to the features of interest.

The resulting test set is suitable for testing under ideal conditions. In practice, however, testing errors do occur. Thus, using the system 100 in the context of testing hearing, the hearing-impaired patient is tested with a few redundant phonemes in order to compensate for testing errors. Moreover, a patient may have hearing loss only in particular frequency ranges, which may not be evident from feature analysis. Thus, the testing uses redundant phonemes to mitigate these problems.

The phonemes are selected based on the patient's weaknesses. In the first test, all fourteen phonemes are presented, since initially there is no assessment of the patient's weaknesses. In the next two tests, eleven phonemes (three from each of the three sets described above) are presented. In the fourth test onwards, eight phonemes (two from each of the three sets) are presented. In the second and third tests, two phonemes from each set are chosen based on the patient's performance model, which captures the feature errors in the previous test. The remaining one phoneme from each set is chosen randomly from the remaining two phonemes. From the fourth test onwards, one phoneme from each set is chosen based on the patient's performance model, while the other phoneme is chosen randomly from the remaining three phonemes. The strategy is summarized as follows:

| Phoneme Sets | Test 1      | Tests 2 and 3                         | Test 4 and subsequent                 |
|--------------|-------------|---------------------------------------|---------------------------------------|
| {m}          | m           | m                                     | m                                     |
| {n}          | n           | n                                     | n                                     |
| {b, p, v, f} | b, p, v, f  | choose 3 of which one randomly        | choose 2 of which one randomly        |
| {t, s, d, z} | t, s, d, z  | choose 3 of which one randomly        | choose 2 of which one randomly        |
| {k, g, sh, j}| k, g, sh, j | choose 3 of which one randomly        | choose 2 of which one randomly        |

Figure 2:
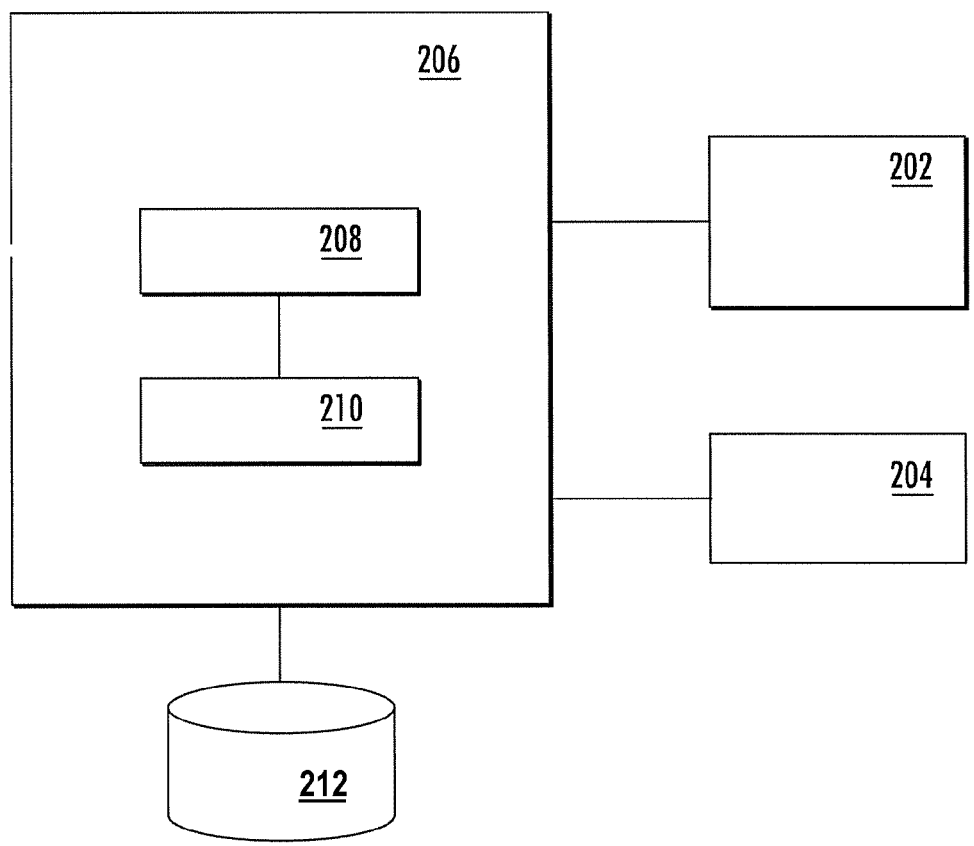
FIG. 2 is a schematic diagram of a system of testing a hearing-impaired patient, according to another embodiment of the invention.

FIG. 2 is a schematic diagram of a computer-based system 200 for testing a hearing-impaired patient, according to another embodiment of the invention. The system 200 illustratively includes an audio unit 202, for audibly presenting a plurality of phonemes to the patient, wherein each phoneme is selected from one of a plurality of phoneme sets corresponding to a predetermined feature selected for testing a hearing capability of the patient. The system 200 further includes a testing unit 206 comprising at least one processor 208 for executing the procedures described above in generating assessments of the hearing capability of the patient based upon patient responses to the audibly-presented phonemes.

The audio unit 202 can comprise, for example, a speaker, headphones, or other electromechanical transducer (not explicitly shown) for generating sound signals that can be played or otherwise rendered to the patient. In different embodiments, the audio unit 202 can be a hearing-enhancement device, a telephone, wireless phone, cellular phone, or the like.

The audio unit 202 can optionally include a microphone or other acoustical transducer for converting audible responses of the patient into electrical signals that are conveyed to the testing unit 206. The system 200 can optionally include a separate patient-response device 204, such as a hand-held push-button device, a keypad or the like that can be used by the patient in response to audibly-presented phonemes. The purpose of these different arrangements is to permit the system 200 to present the plurality of phonemes to which the patient responds so as to assess hearing capabilities of the patient. Optionally, the system 200 can also include a recorder 210 for recording the audible responses or signals conveyed to the testing unit 206 by the patient using the optional patient-response device 204.

Operatively, the testing unit 206 generates a first assessment of the hearing capability of the patient based upon a response of the patient to each audibly presented phoneme, according to the procedures described above. The system 200, subsequently, audibly presents a second plurality of phonemes to the patient and generates a second assessment of the hearing capability of the patient based upon patient response. The second plurality of phonemes is selected by the testing unit 206 choosing at least one less phoneme from each phoneme set that contains more than one phoneme, one of the phonemes selected from each phoneme set containing more than one phoneme being selected randomly by the testing unit.

The system 200 optionally can include one or more databases 212 for storing the plurality of phonemes. Although, the audio unit 202 is shown as communicatively linked directly, wirelessly or through a wire-line connection, with the testing unit 206, it will be readily apparent to one skilled in the relevant art that the system can be communicatively linked to the audio unit through one or more intermediate communication nodes of voice-based network or data communications network, such as the Internet.

Figure 3:
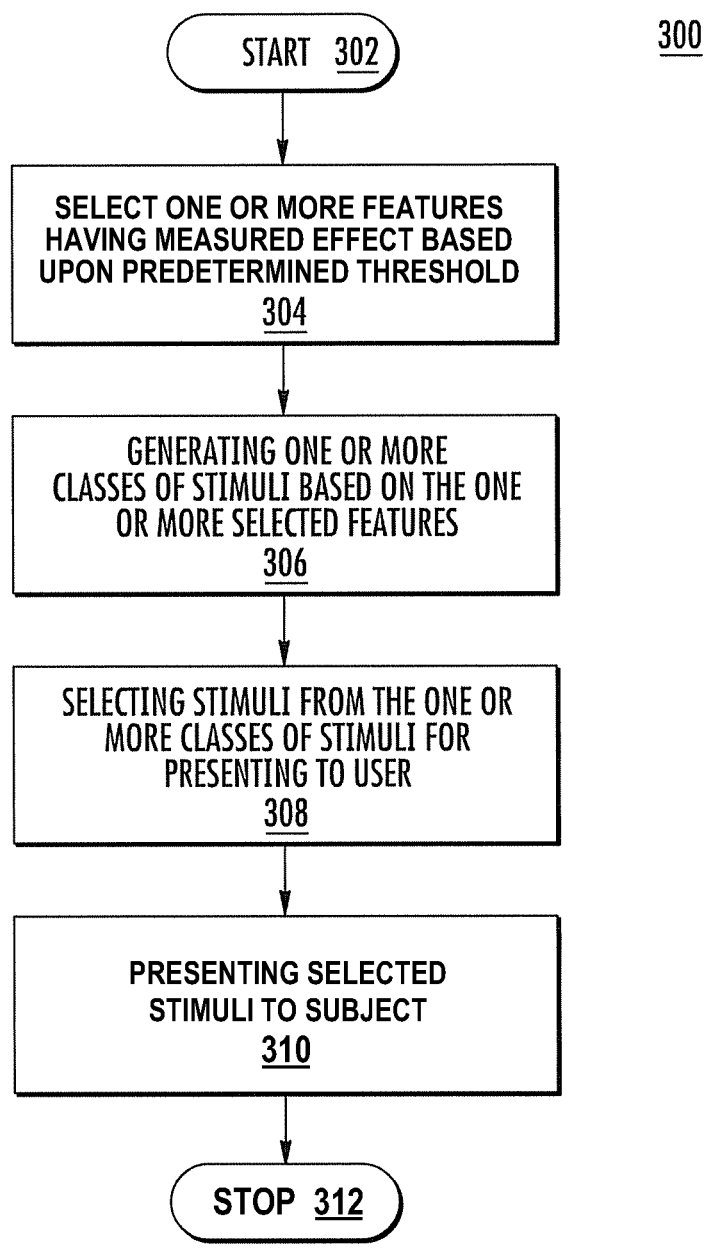
FIG. 3 is a flowchart of exemplary steps in a method for generating a test set for testing a subject, according to yet another embodiment of the invention.

FIG. 3 illustrates certain method aspects of the invention. FIG. 3 is a flowchart of exemplary steps in a method 300 of generating a test set for testing a subject using a computer system comprising logic-based processing circuitry. The method 300 illustratively includes, after start at block 302, selecting one or more features from among a plurality of features at block 304. The selecting, more particularly comprises selecting one or more feature having a measurable effect on the subject, as determined based on a predetermined threshold. The method 300 further includes generating one or more classes of stimuli based on the selected features at block 306. Additionally, the method includes selecting stimuli from one or more of the classes at block 308 and presenting the selected stimuli to the subject at block 310. The method illustratively concludes at block 312.

In another embodiment, a method of generating a test set for testing a subject using a computer system comprising logic-based processing circuitry includes selecting one or more features from among a plurality of features, wherein a measurable effect on the subject of each feature selected exceeds a predetermined threshold. Additionally, the method includes generating one or more classes of stimuli based on the selected features. The method further includes selecting stimuli from one or more of the classes for presenting to the subject, wherein selecting comprises choosing a stimulus from a class to present to the subject, and subsequently selecting at least one less from each class that comprises more than one stimulus.

Still another embodiment of a method for generating a test set for testing a subject using a computer system comprising logic-based processing circuitry includes selecting one or more features from among a plurality of features, wherein a measurable effect on the subject of each feature selected exceeds a predetermined threshold, and based on the selected features, generating one or more classes of stimuli. The method further includes selecting stimuli from each class for presenting to the subject, wherein selecting comprises initially choosing each stimulus from each class to present to the subject, and subsequently selecting at least one less from each class that comprises more than one stimulus, at least one of the stimuli subsequently selected from each class that comprises more than one stimulus being selected randomly.

The invention, as already noted, can be realized in hardware, software, or a combination of hardware and software. The invention can be realized in a centralized fashion in one computer system or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, as also already noted, can be embedded in a computer program product, which comprises all the features enabling the implementation of the methods described herein and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The foregoing description of preferred embodiments of the invention has been presented for the purposes of illustration. The description is not intended to limit the invention to the precise forms disclosed. Indeed, modifications and variations will be readily apparent from the foregoing description. Accordingly, it is intended that the scope of the invention not be limited by the detailed description provided herein.

We claim:

1. A computer-implemented method for generating a test set for testing a subject using a computer system comprising logic-based processing circuitry, the method comprising:
    selecting at least one feature from among a plurality of features, wherein the at least one feature is selected based upon a measure of the role of the at least one feature in determining the subject's hearing ability;
    based on the at least one selected feature, generating one or more classes of stimuli;
    presenting at least one stimulus from the one or more classes of stimuli to a subject;
    modifying at least one of the one or more classes, wherein modifying at least one of the one or more classes comprises randomly removing a stimulus from at least one of the one or more classes to generate one or more modified classes;
    presenting at least one stimulus from the one or more modified classes; and
    adjusting at least one operational parameter of a hearing-enhancement device based at least in part on a hearing performance of the patient with respect to different parameter values.

2. The method of claim 1, further comprising selecting at least one stimulus associated with a non-selected feature to present to the subject.

3. The method of claim 2, wherein selecting at least one stimulus associated with a non-selected feature is repeated iteratively.

4. The method of claim 3, wherein iteratively selecting at least one stimulus associated with a non-selected feature comprises selecting one less stimulus from a class comprising more than one stimulus.

5. The method of claim 4, wherein the at least one stimulus associated with a non-selected feature is randomly selected.

6. The method of claim 1, further comprising initially presenting each of a predetermined number of stimuli prior to selecting from among the plurality of features associated with each of the predetermined number of stimuli.

7. The method of claim 6, wherein selecting from among the plurality of features further comprises computing for a feature a product equal to a value assigned to the feature times a number of stimuli influenced by the feature.

8. The method of claim 1, further comprising determining a measure of significance of each class of stimuli on assessing the hearing capability of the subject.

9. The method of claim 8, wherein the measure of significance of the $i^{th}$ class is equal to $$\overline{p}_i = \begin{cases} \dfrac{1}{n_i}\sum_{j=1}^{n_i} P_{ij} & \text{if } n_i > 0 \\ 0 & \text{otherwise} \end{cases}$$

where $n_i$ is the number of stimuli contained in the $i^{th}$ class, and $P_{ij}$ is an empirically determined value based upon an assessment of subject responses to administered stimuli.

10. The method of claim 1, further comprising determining the number of times to present different stimuli to the subject based upon a computed measure of subject hearing weakness, the measure, $s_i$, being defined as $$s_i = \left\lceil k \times \dfrac{e_i}{\sum_{j=1}^{c} e_j} \right\rceil$$

wherein $e_i$ is a number of stimuli selected from the $i^{th}$ class and erroneously recognized by the subject, wherein $c$ is a number of stimuli contained in the $i^{th}$ class, and where $k$ is a predetermined constant.

11. A computer-implemented method of testing a hearing-impaired patient using a computer system including logic-based processing circuitry, the method comprising:
  audibly presenting a first plurality of phonemes to the patient, wherein the first plurality consists of at least one phoneme from each of a plurality of preexisting phoneme sets, each preexisting phoneme set corresponding to a predetermined feature selected for testing a hearing capability of the patient;
  based on a response of the patient to each audibly presented phoneme, generating a first assessment of the hearing capability of the patient;
  audibly presenting a second plurality of phonemes to the patient and generating a second assessment of the hearing capability of the patient based on patient response, wherein the second plurality of phonemes consists of at least one less phoneme than the first plurality of phonemes, wherein the at least one less phoneme is selected at random; and
  adjusting at least one operational parameter of a hearing-enhancement device based at least in part on a hearing performance of the patient with respect to different parameter values.

12. The method of claim 11, wherein the second plurality of phonemes is created by eliminating from the first plurality of phonemes one phoneme from each of the plurality of preexisting phoneme sets that comprise more than one phoneme, and further comprising audibly presenting a third plurality of phonemes, wherein the third plurality of phonemes is created by eliminating from the first plurality of phonemes two phonemes from each of the plurality of preexisting phoneme sets that comprise more than two phonemes, wherein the two phonemes are selected at random.

13. A computer-based system for generating a test set for testing a subject, the system comprising:
  at least one processor;
  an electronic memory having stored therein electronic data representing a plurality of features for testing a particular capability of the subject;
  said at least one processor configured to select at least one feature from among the plurality of features, wherein the at least one feature is selected based upon a measure of the role of the at least one feature in determining the subject's hearing ability; and
  said at least one processor configured to:
  generate one or more classes of stimuli based upon the at least one selected feature;
  present at least one stimulus from the one or more classes of stimuli to a subject;
  modify at least one of the one or more classes, wherein modifying at least one of the one or more classes comprises randomly removing a stimulus from at least one of the one or more classes to generate one or more modified classes;
  present at least one stimulus from the one or more modified classes; and
  adjusting at least one operational parameter of a hearing-enhancement device based at least in part on a hearing performance of the patient with respect to different parameter values.

14. The system of claim 13, wherein said at least one processor is further configured to select at least one stimulus associated with a non-selected feature to present to the subject.

15. The system of claim 14, wherein said at least one processor is configured to iteratively select at least one stimulus associated with a non-selected feature.

16. The system of claim 15, wherein said at least one processor is configured to iteratively select at least one stimulus associated with a non-selected feature by, at least in part, selecting one less stimulus from a class comprising more than one stimulus.

17. The system of claim 15, wherein said at least one processor is configured to iteratively select at least one stimulus associated with a non-selected feature by, at least in part, randomly selecting the at least one stimulus.

18. The system of claim 13, wherein the system is configured to initially present each of a predetermined number of stimuli prior to selecting from among the plurality of features associated with each of the predetermined number of stimuli.

19. The system of claim 18, wherein said at least one processor is configured to select from among the plurality of features by computing for a feature a product equal to a value assigned to the feature times a number of stimuli influenced by the feature.

20. The system of claim 13, wherein said at least one processor is further configured to determine a measure of significance of each class of stimuli on assessing the hearing capability of the subject.

21. The system of claim 20, wherein the measure of significance is equal to $$\overline{p}_i = \begin{cases} \dfrac{1}{n_i}\sum_{j=1}^{n_i} P_{ij} & \text{if } n_i > 0 \\ 0 & \text{otherwise} \end{cases}$$

where $n_i$ is the number of stimuli contained in the $i^{th}$ class, and $P_{ij}$ is an empirically determined value based upon an assessment of subject responses to administered stimuli.

22. The system of claim 13, wherein said at least one processor is further configured to determine a number of times to present different stimuli to the subject based upon a computed measure of subject hearing weakness, the measure, $s_i$, defined as $$s_i = \left\lceil k \times \dfrac{e_i}{\sum_{j=1}^{c} e_i} \right\rceil$$

wherein $e_i$ is a number of stimuli selected from the $i^{th}$ class and erroneously recognized by the subject, wherein c is a number of stimuli contained in the $i^{th}$ class, and where k is a predetermined constant.

23. A computer-based system of testing a hearing-impaired patient, the system comprising:
  at least one processor;
  memory encoding processor-executable instructions perform operations comprising:
    creating a first set of phonemes, wherein the first set of phonemes comprises one or more phonemes from a plurality of preexisting phoneme sets, wherein at least one of the preexisting phoneme sets comprises a plurality of phonemes, and wherein at least one of the preexisting phoneme sets corresponds to a predetermined feature selected for testing a hearing capability of the hearing-impaired patient;

creating a second set of phonemes by eliminating at least one phoneme from each of the first set of preexisting phoneme sets;

randomly selecting at least one phoneme from the second plurality of phonemes from each class that comprises more than one phonemes;

audibly presenting a plurality of phonemes from the first set of phonemes and the second set of phonemes to the hearing-impaired patient;

generating an assessment of the hearing capability of the hearing-impaired patient based upon a response of the hearing-impaired patient to the audibly presented plurality of phonemes; and adjusting at least one operational parameter of a hearing-enhancement device based at least in part on the generated assessment.

24. A non-transitory computer-readable medium having embedded therein computer-executable code that, when executed by at least one processor, perform a method comprising:

selecting at least one feature from among a plurality of features, wherein the at least one feature is selected based upon a measure of the role of the at least one feature in determining a subject's hearing ability;

based at least upon the at least one selected feature, generating one or more classes of stimuli;

presenting at least one stimulus from the one or more classes of stimuli to a subject;

modifying at least one of the one or more classes, wherein modifying at least one of the one or more classes comprises randomly removing a stimulus from at least one of the one or more classes to generate one or more modified classes;

presenting at least one stimulus from the one or more modified classes; and adjusting at least one operational parameter of a hearing-enhancement device based at least in part on a hearing performance of the patient with respect to different parameter values.

25. A computer-implemented method for generating a test set for testing a subject using a computer system comprising logic-based processing circuitry, the method comprising:

selecting one or more features from among a plurality of features, wherein the one or more features are selected based upon a measure of a role of the one or more selected features in determining the subject's hearing ability;

based at least upon the one or more selected features, generating at least one class of stimuli;

presenting at least one stimulus from the at least one class of stimuli to a subject;

modifying the at least one class, wherein modifying at the least one class comprises randomly removing a stimulus from the at least one class to generate at least one modified class of stimuli;

presenting at least one stimulus from the at least one modified class; and adjusting at least one operational parameter of a hearing-enhancement device based at least in part on a hearing performance of the patient with respect to different parameter values.

* * * * *